(12) United States Patent
Ito

(10) Patent No.: US 6,702,738 B2
(45) Date of Patent: Mar. 9, 2004

(54) PORTABLE ENDOSCOPE WITH LIQUID AND GAS SUPPLY APPARATUS

(75) Inventor: Shunichi Ito, Tokyo (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 10/231,124

(22) Filed: Aug. 30, 2002

(65) Prior Publication Data

US 2003/0045779 A1 Mar. 6, 2003

(30) Foreign Application Priority Data

Aug. 31, 2001 (JP) ...................... P2001-263039

(51) Int. Cl.[7] ................................................ A61B 1/12
(52) U.S. Cl. ...................................... 600/158; 600/156
(58) Field of Search ............................... 600/156, 158, 600/159, 157

(56) References Cited

U.S. PATENT DOCUMENTS

| | | | | |
|---|---|---|---|---|
| 4,258,721 A | * | 3/1981 | Parent et al. ............... | 600/158 |
| 5,630,783 A | * | 5/1997 | Steinberg .................... | 600/158 |
| 5,674,183 A | * | 10/1997 | Adachi ........................ | 600/158 |
| 2003/0032862 A1 | * | 2/2003 | Ota et al. .................... | 600/158 |
| 2003/0040658 A1 | * | 2/2003 | Sano et al. .................. | 600/158 |

* cited by examiner

*Primary Examiner*—John Mulcahy
(74) *Attorney, Agent, or Firm*—Greenblum & Bernstein, P.L.C.

(57) ABSTRACT

A portable endoscope has a liquid supplying tube that transmits liquid to the tip of the endoscope, a container that is spatially connected to the liquid supplying tube and stores the liquid, a gas supplying tube that is connected to an inside space of the container and transmits gas to the tip of the endoscope, a liquid and gas supplier that supplies the liquid in the container to the liquid supplying tube and supplies the gas to the gas supplying tube, and a holder that holds the container such that the container generally keeps a horizontal position.

13 Claims, 8 Drawing Sheets

PORTABLE ENDOSCOPE WITH LIQUID AND GAS SUPPLY APPARATUS

BACKGROUND OF THE INVENTION

1. Field of the Invention

The present invention relates to an endoscope with a liquid and gas supply apparatus that supplies liquid and gas, such as water and air, to the tip of an endoscope.

2. Description of the Related Art

A liquid and gas supply apparatus, which has a bottle and pump, is usually incorporated in a light source apparatus for a fiber-scope or an electronic endoscope system including a video-scope with an image sensor and a video-processor. In the video-scope/fiber-scope, a liquid (water) supplying tube and a gas (air) supplying tube are provided. The bottle is spatially connected to the liquid supplying tube and the pump is spatially connected to the gas supplying tube. Generally, water is stored in the bottle, whereas the pump takes in and compresses fresh air and sends the compressed air to the tip.

To wash an objective lens provided in the tip of the fiber-scope/video-scope, or to remove obstructions on an observed portion, the air or water is discharged from the tip of the fiber-scope/video-scope. When supplying the air, the compressed air flows in the air supplying tube and is then discharged from the tip of the fiber-scope/video-scope. On the other hand, when supplying the water, the compressed air is directed to the inside of the bottle, where the water surface is pressed due to the pressure of the compressed air. The water in the bottle is pumped out, and flows in the water supplying tube so that the water is discharged from the tip of the fiber-scope/video-scope.

Further, medicinal liquid for inspecting the diseased portion, nitrogen for expanding the inside of the digestive organ, and oxygen for the bronchial tubes are dischargeable via the water supplying tube or the air supplying tube.

In the case of the conventional construction of the liquid and gas supply apparatus, when the bottle inclines, water can flow through the air supplying tube and can be unexpectedly discharged from the tip. Further, a conventional liquid and gas supply apparatus mounted on a desk or table is not suitable for a portable endoscope having an internal light source, because the portability is greatly reduced.

SUMMARY OF THE INVENTION

Therefore, an object of the present invention is to provide a portable endoscope that is capable of supplying liquid and gas without restricting portability, and that prevents unexpected discharge of liquid.

A portable endoscope according to the present invention has a liquid supplying tube, a container, a gas supplying tube, a liquid and gas supplier, and a holder. The liquid supplying tube transmits liquid to the tip of the endoscope so that the liquid is discharged from the tip of the endoscope. The container is spatially connected to the liquid supplying tube and stores the liquid. For example, the container is formed as a bottle having a narrow neck and mouth. The gas supplying tube is connected to an inside space of the container and transmits gas to the tip of the endoscope so that the gas is discharged from the tip of the endoscope. The liquid and gas supplier supplies the liquid in the container to the liquid supplying tube and supplies the gas to the gas supplying tube. The holder supports or holds the container such that the container generally keeps a horizontal position. The horizontal position indicates a position in a situation that the container is placed on a level surface. When the container is formed in a bottle, the bottom of the bottle is a plane perpendicular to the vertical direction so that the bottom surface is always parallel to the level surface.

Preferably, the holder allows the container to be pivotable in accordance with gravity, which operates on the container with the liquid. For example, the holder has a flexible tube, a universal joint, or a ball joint.

A portable endoscope according to another aspect of the present invention has a liquid supplying tube that transmits liquid to the tip of the endoscope, a container that is spatially connected to the liquid supplying tube and stores the liquid, a gas supplying tube that is connected to an inside space of the container and transmits gas to the tip of the endoscope, a liquid and gas supplier that supplies the liquid in the container to the liquid supplying tube and supplies the gas to the gas supplying tube, and a holder that holds the container. While the operator manipulates the endoscope, the holder holds or supports the container such that the container keeps one predetermined position with respect to the vertical direction.

BRIEF DESCRIPTION OF THE DRAWINGS

The present invention will be better understood from the description of the preferred embodiment of the invention set fourth below together with the accompanying drawings, in which.

DESCRIPTION OF THE PREFERRED EMBODIMENTS

Hereinafter, the preferred embodiments of the present invention are described with reference to the attached drawings.

Figure 1:
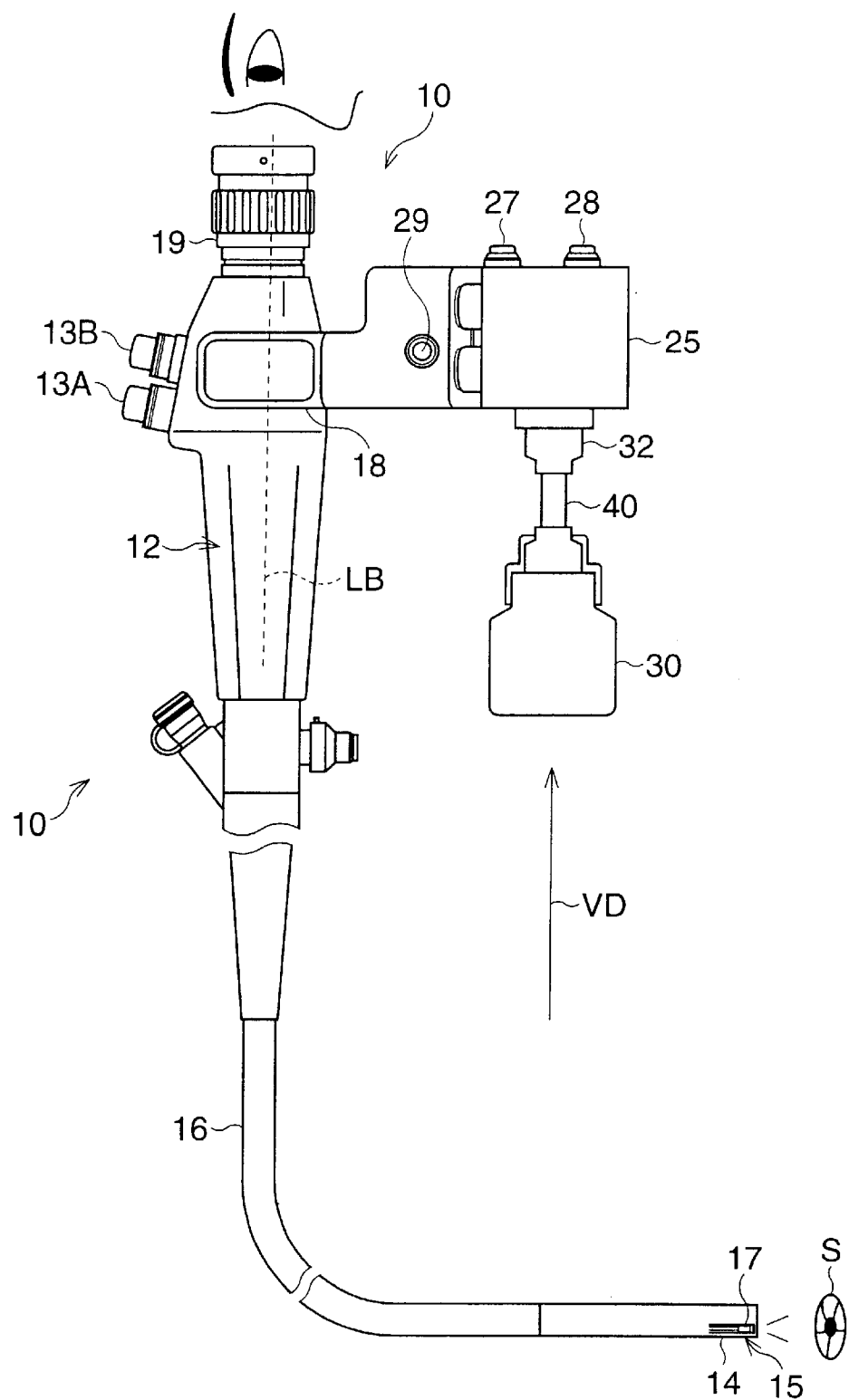
FIG. 1 is a schematic plan view of a portable endoscope according to the first embodiment.

FIG. 1 is a schematic plan view of a portable endoscope according to a first embodiment.

A fiber-scope 10 is a portable type endoscope with an internal light source, and has a tip portion 15, a bending portion 14, an inserting portion 16, an operating portion 12, an eyepiece 19, and a connecting arm 18. Further, the fiber-scope 10 has a water and air supply apparatus 25, which is connected to the connecting arm 18. When an operation or inspection is started, the inserting portion 16 is inserted into an inner organ, such as the stomach.

A plurality of LEDs (herein, one LED is shown) 17 for illuminating a subject S is provided at the tip portion 15.

When a lamp switch button 27 is turned ON, the plurality of LEDs 17 emits light, which is radiated from the tip portion 15. Consequently, the subject S is illuminated by the light. Light reflected on the subject S passes through an objective lens (not shown) provided in the tip portion 15, and reaches an incident surface of an image fiber-optic bundle (not shown). Thus, the subject image is formed on the incident surface. The image fiber-optic bundle is provided for optically transmitting the subject image and extends from the tip portion 15 to the eyepiece 19. The optically transmitted subject image is formed at the eyepiece, thus the operator can observe the subject S via the eyepiece 19.

To wash the objective lens and remove dirt, or any obstructions on the subject S, water and air supplying tubes (herein, not shown) are provided in the fiber-scope 10. They extend from the tip portion 15 to a water and air supplying switch button 13A, to discharge the water or air from the tip portion 15 of the fiber-scope 10. The water and air supply apparatus 25 supplies the water/air to the water and air supplying tubes. A bottle 30 is cylindrical and is connected to the connecting portion 32 of the water and air supply apparatus 25 via a flexible tube 40. When a pump switch button 28 provided on the water and air supply apparatus 25 is pressed, a pump (herein, not shown) operates. Then, as described later, when the water and air supplying switch 13A is operated, air or water in the bottle 30 is discharged from the tip portion 15.

A forceps channel (not shown) is further provided in the fiber-scope 10, and is connected to an absorbing, or suction unit (not shown) via an inlet 29 of the connecting arm 18. When an absorbing switch button 13B is operated, the obstruction on the subject S is sucked up and is then fed to the absorbing unit. While the fiber-scope 10 is operated by the operator, the longitudinal direction LB of the fiber-scope 10 generally becomes parallel to the vertical direction VD.

Figure 2:
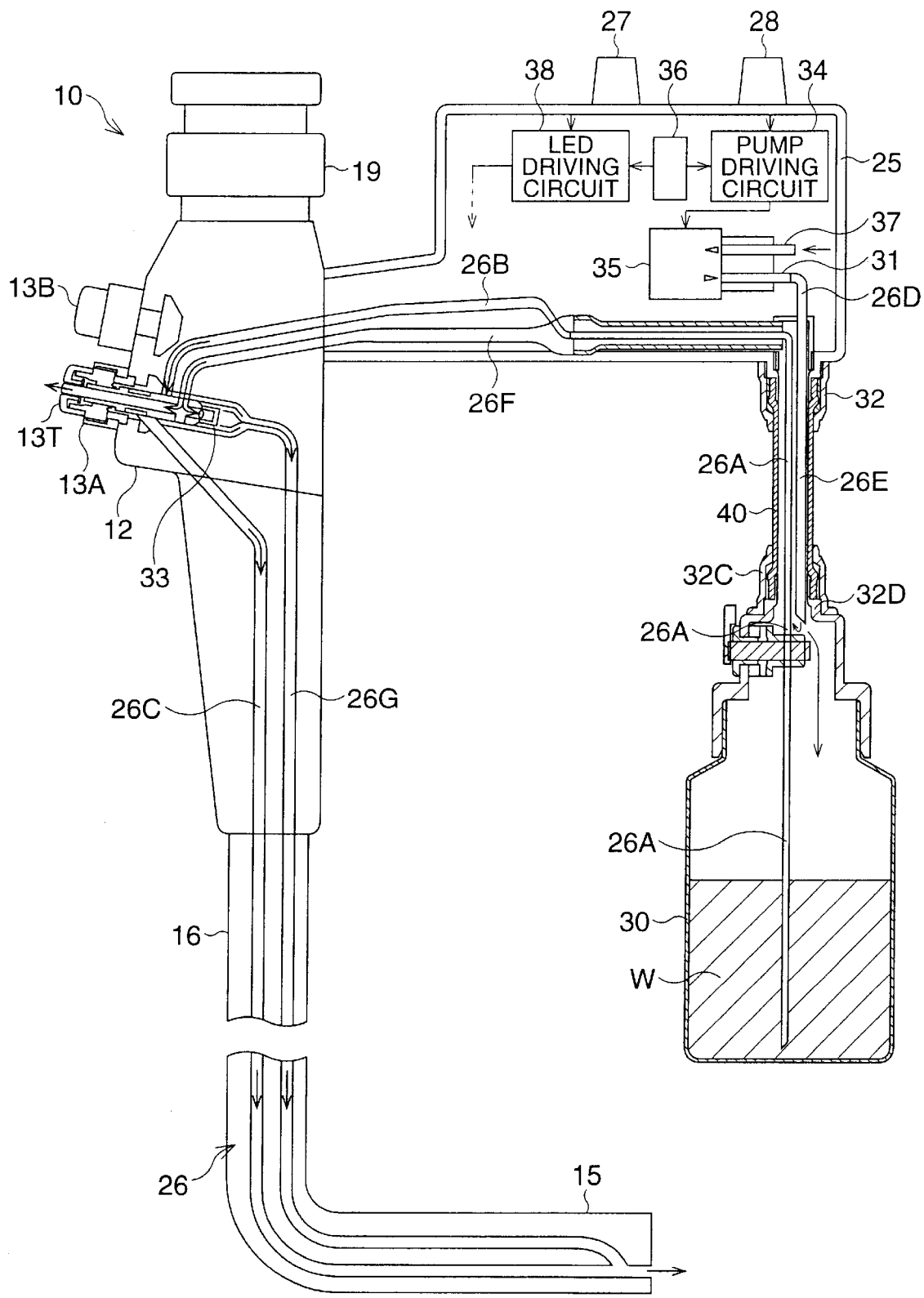
FIG. 2 is a view schematically showing an inner construction of the fiber-scope.

FIG. 2 is a view schematically showing an inner construction of the fiber-scope 10.

A battery 36 provided in the water and air supply unit 25 supplies electric power to an LED driving circuit 38 for driving the LEDs 17, and to a pump driving circuit 34 for driving the pump 35. When the lamp switch button 27 is turned ON/OFF, the LED driving circuit 38 turns ON/OFF the LEDS 17. When the pump switch button 28 is pressed, the pump driving circuit 34 drives/suspends the pump 35.

The water and air supplying tubes 26 have water supplying tubes 26A, 26B, 26C and air supplying tubes 26D, 26E, 26F, and 26G. The air supplying tube 26D extends from the pump 35 to the inside of the bottle 30, which is spatially connected to the air supplying tube 26D via the air supplying tube 26E in the flexible tube 40, the air supplying tube 26F in the connecting arm 18, and the water and air supplying switch button 13A.

The water supplying tube 26A extends from the tube connecting portion 32 to the inside of the bottle 30, and is spatially connected to the water supplying tube 26C via the bottle 30, the water supplying tube 26B in the connecting arm 18, and the water and air supplying switch button 13A. The flexible tube 40 is formed along the circumference of the air supplying tube 26E such that the flexible tube 40 coats the air supplying tube 26E. In the air supplying tube 26E, the water supplying tube 26A and the air supplying tube 26D extend to the bottle 30. The bottle 30 is cylindrical, and a mouth 32D of the bottle 30 is covered with a cap 32C. The water supplying tube 26A passes through the center of the bottle 30 and extends to the bottom of the bottle 30.

The pump 35 takes in fresh air and discharges compressed air. An intake tube 37 extends to a hole (not shown) formed in an outer surface of the operating portion 12. A discharging tube 31, from which the compressed air is discharged, is spatially connected to the air supplying tube 26D. When the pump 34 operates, the compressed air flows in the air supplying tube 26D toward the bottle 30.

A valve 33 is provided at the water and air supplying switch button 13A. When the water and air supplying switch button 13A is not covered by the thumb of the operator, the valve 33 intercepts, or closes the spatial connection between the air supplying tube 26G and the air supplying tube 26F, and discharges the compressed air, transmitted from the pump 34, from the top portion 13T of the water and air supplying switch button 13A. Namely, the compressed air is not supplied to the tip portion 15. Further, the valve 33 closes the spatial connection between the water supplying tube 26C and the water supplying tube 26B, hence water is not supplied.

When supplying air, the thumb of the operator is placed on the top portion 13T of the water and air supplying switch button 13A. The position of the valve 33 is shifted toward the opposite side of the top portion 13A by the backflow of air, so that the air supplying tube 26F is spatially connected to the air supplying tube 26G. Thus, the compressed air flows through the air supplying tube 26G and is discharged from the tip portion 15.

When supplying water, the water and air supplying switch button 13A is pressed by the thumb of the operator. The position of the valve 33 is further shifted by the pressing, which spatially closes the air supplying tube 26G and the air supplying tube 26F, and spatially connects the water supplying tube 26C and the water supplying tube 26B. Consequently, the compressed air from the pump 34 flows to the inside of the bottle 30. The water W in the bottle 30 is pressed by the compressed air so that the water W flows in the water supplying tubes 26A, 26B, the water and air supplying switch button 13A, and the water supplying tube 26C, and is then discharged from the tip portion 15.

Note that, the construction of the water and air supplying switch button 13A having the valve 33, described above, is well known in the prior art.

Figure 3:
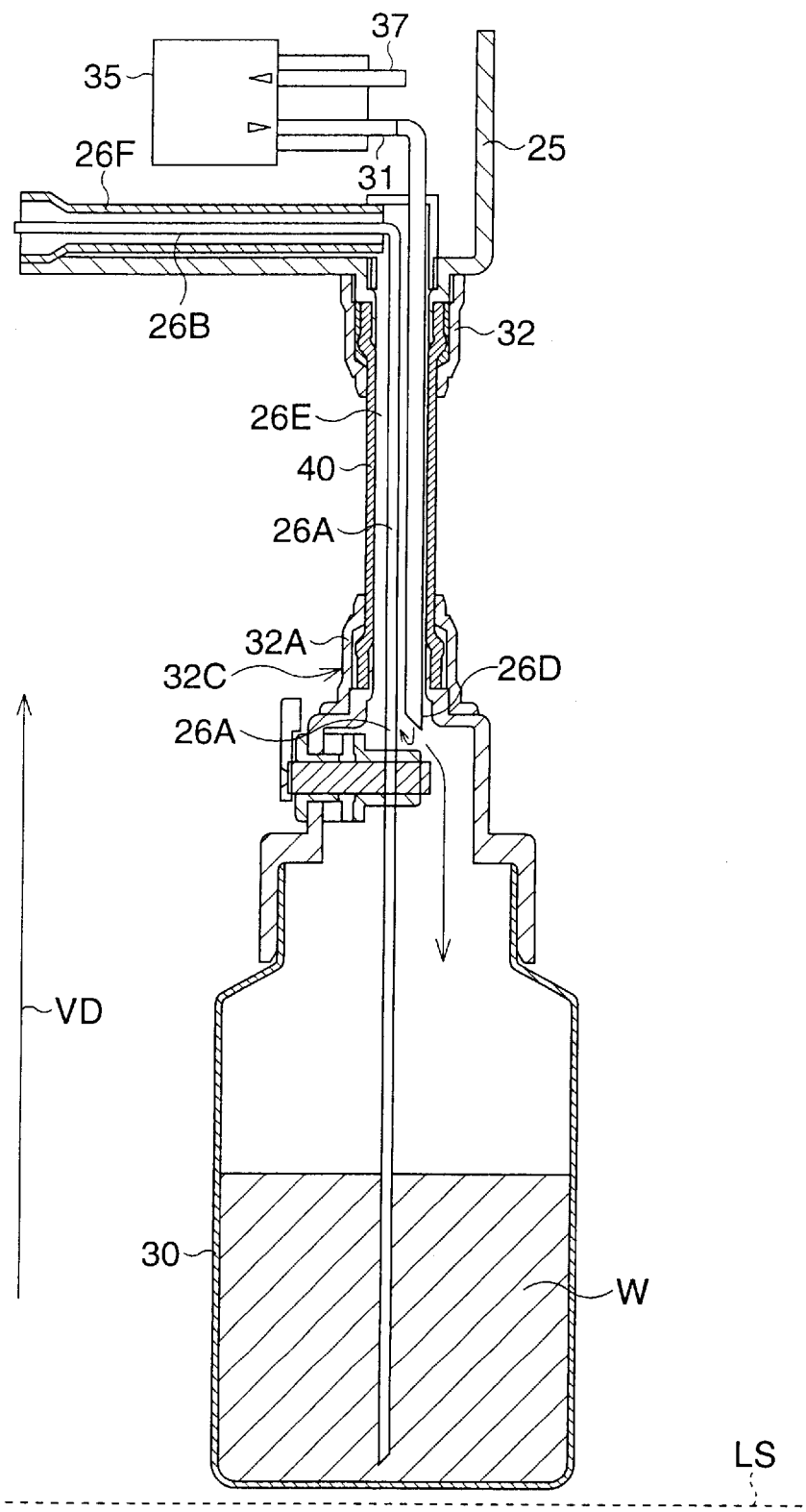
FIG. 3 is a view showing the position of the water and air supply apparatus and the position of the bottle.
Figure 4:
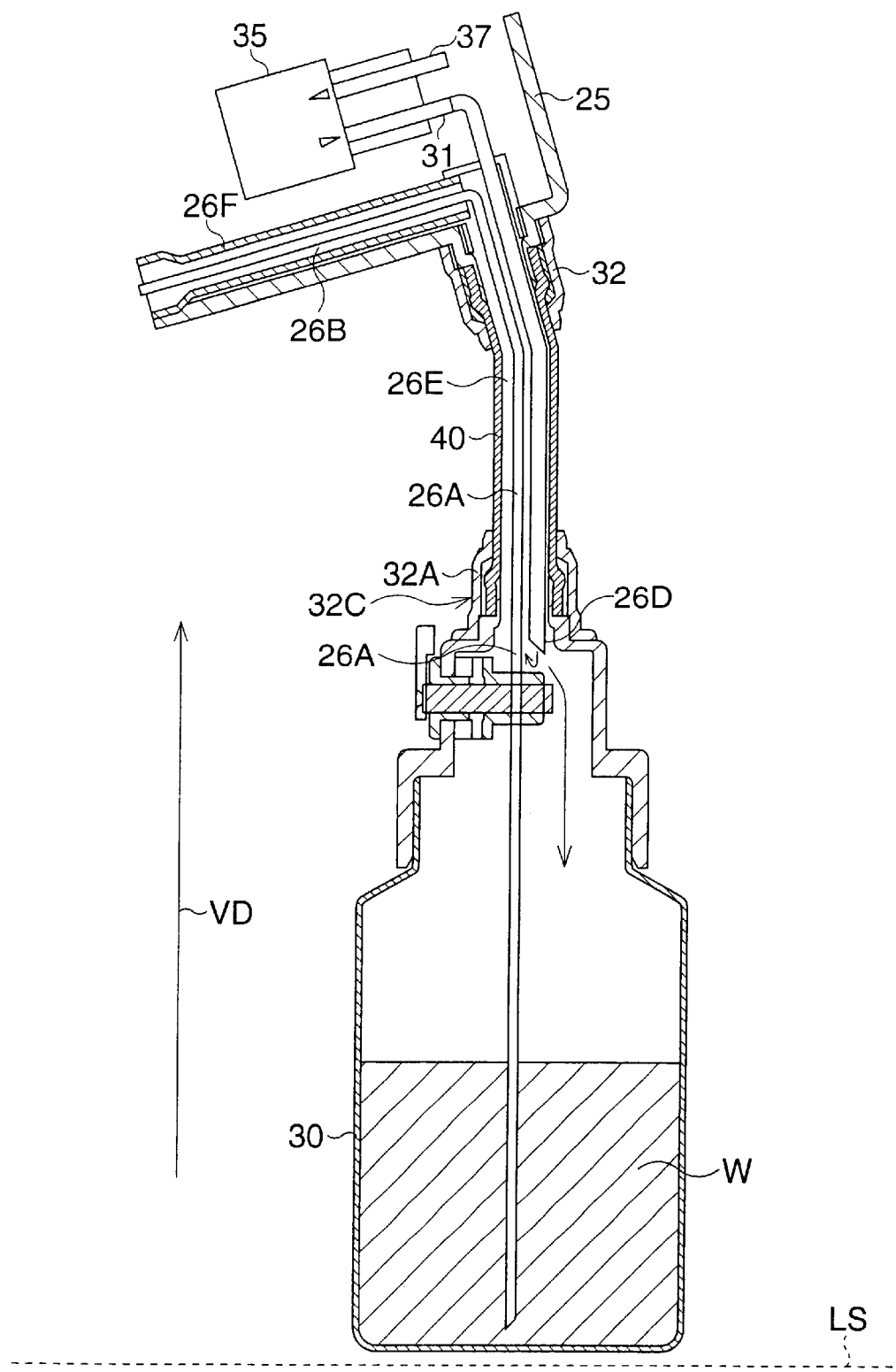
FIG. 4 is a view showing the position of the water and air supply apparatus and the position of the bottle in a situation that the position of the endoscope is changed.

FIG. 3 is a view showing the position of the water and air supply apparatus 25 and the position of the bottle 30. FIG. 4 is a view showing the position of the water and air supply apparatus 25 and the position of the bottle 30 in a situation where the position of the endoscope is changed.

The flexible tube 40 is composed of soft plastic (for example, silicon). The upper portion of the flexible tube 40 is fixed to the tube connecting portion 32. On the other hand, the lower portion of the flexible tube 40 is fixed to an attachment portion 32A of the cap 32C. The air supplying tubes 26D, 26E and the water supplying tube 26A are also composed of flexible plastic member.

The flexible tube 40 extends along the vertical direction VD, and the bottle 30 is pivotable around the tube connecting portion 32 in accordance with the gravity that operates the bottle 30 including the water W. Accordingly, while the operator manipulates the fiber-scope 10, the bottle 30 always keeps the horizontal position regardless of the position of the water and air supply apparatus 25, namely, the position of the operating portion 12 (See FIG. 4). The bottom of the bottle 30 is always parallel to the level surface LS. In this embodiment, the horizontal position indicates a position in a situation that the bottle 30 is placed on the level surface LS.

In this way, in this embodiment, the bottle 30 is attached to the water and air supply apparatus 25 via the flexible tube 40, which allow the bottle 30 to be pivotable. While the operator manipulates the fiber-scope 10, the bottle 30 keeps the horizontal position so that the water is not discharged erroneously. Thus, the conventional construction according to the water-supply and the air-supply can be directly applied to the portable endoscope.

The flexible tube 40 may be composed of rubber elastic member. The bottle 30 may be attached to a side surface of the operating portion 12 in place of the water and air supply apparatus 25.

In this embodiment, the water-supply and the air-supply are independently controlled by using the water and air supplying switch button 13A with the valve 33. However, other constructions may be applied. For example, the flow of the compressed air may be controlled by a solenoid valve.

Figure 5:
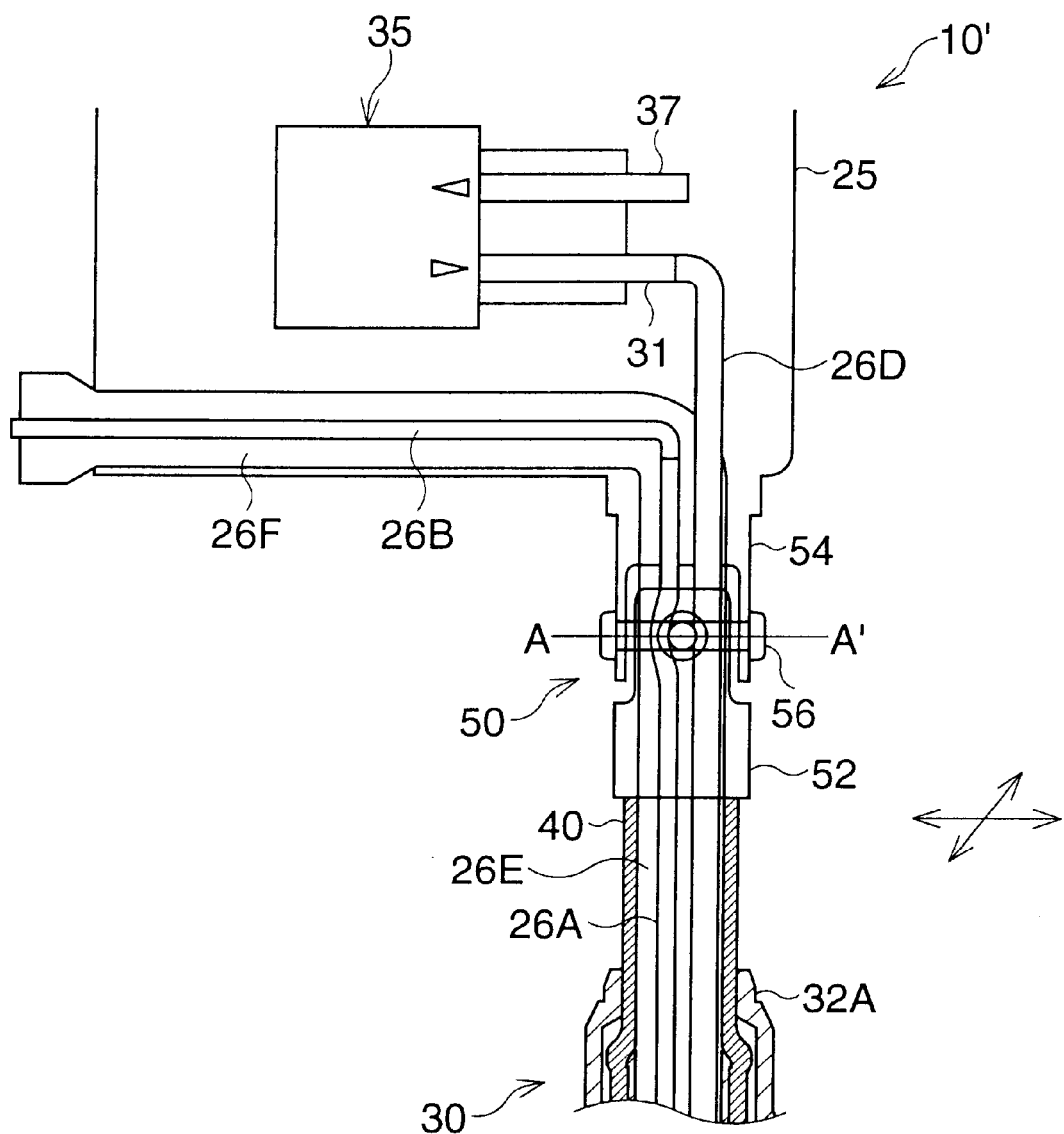
FIG. 5 is a view showing a connecting portion of the bottle and the water and air supply apparatus according to the second embodiment.
Figure 6:
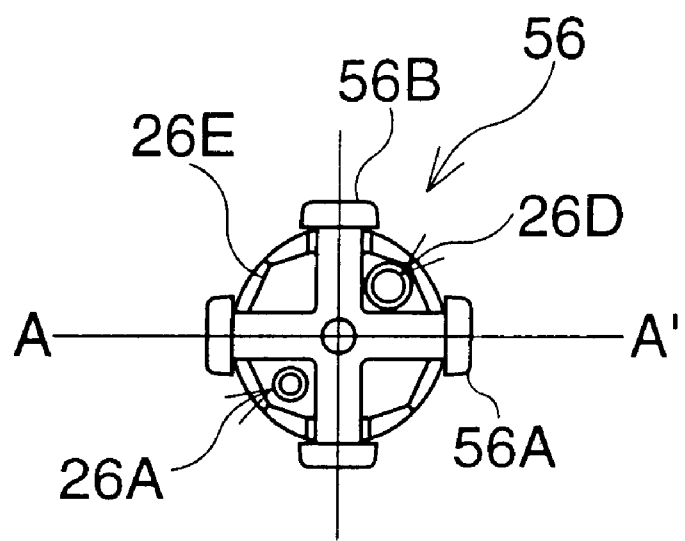
FIG. 6 is a view showing a section view of the connecting portion shown in FIG. 5.

With reference to FIGS. 5 and 6, a second embodiment is explained. The second embodiment is different from the first embodiment in that a universal joint (coupling) is applied.

FIG. 5 is a view showing a connecting portion associated with the bottle. In this embodiment, the bottle 30 is connected to the water and air supply apparatus 25 via a universal joint 50. The universal joint 50 has a first connector 54, which is formed on the body of the water and air supply apparatus 25, a cross-shaped pivot member 56, and a second connector 52, which is connected to the pivot member 56.

FIG. 6 is a section view along line A—A' shown in FIG. 5. The air supplying tube 26D and the water supplying tube 26A extend through the air supplying tube 26E such that the air supplying tube 26D and the water supplying tube 26A do not hit against pivot member 56. A first axial member 56A is rotatably attached to the first connector 54, whereas a second axial member 56B perpendicular to the first axial member 56A is rotatably attached to the second connector 52. Accordingly, while the operator manipulates the fiberscope 10, the bottle 30 is pivotable along a first direction and a second direction. Note, the first direction indicates a direction parallel to the paper (A—A') and the second direction indicates a direction perpendicular to the paper.

Figure 7:
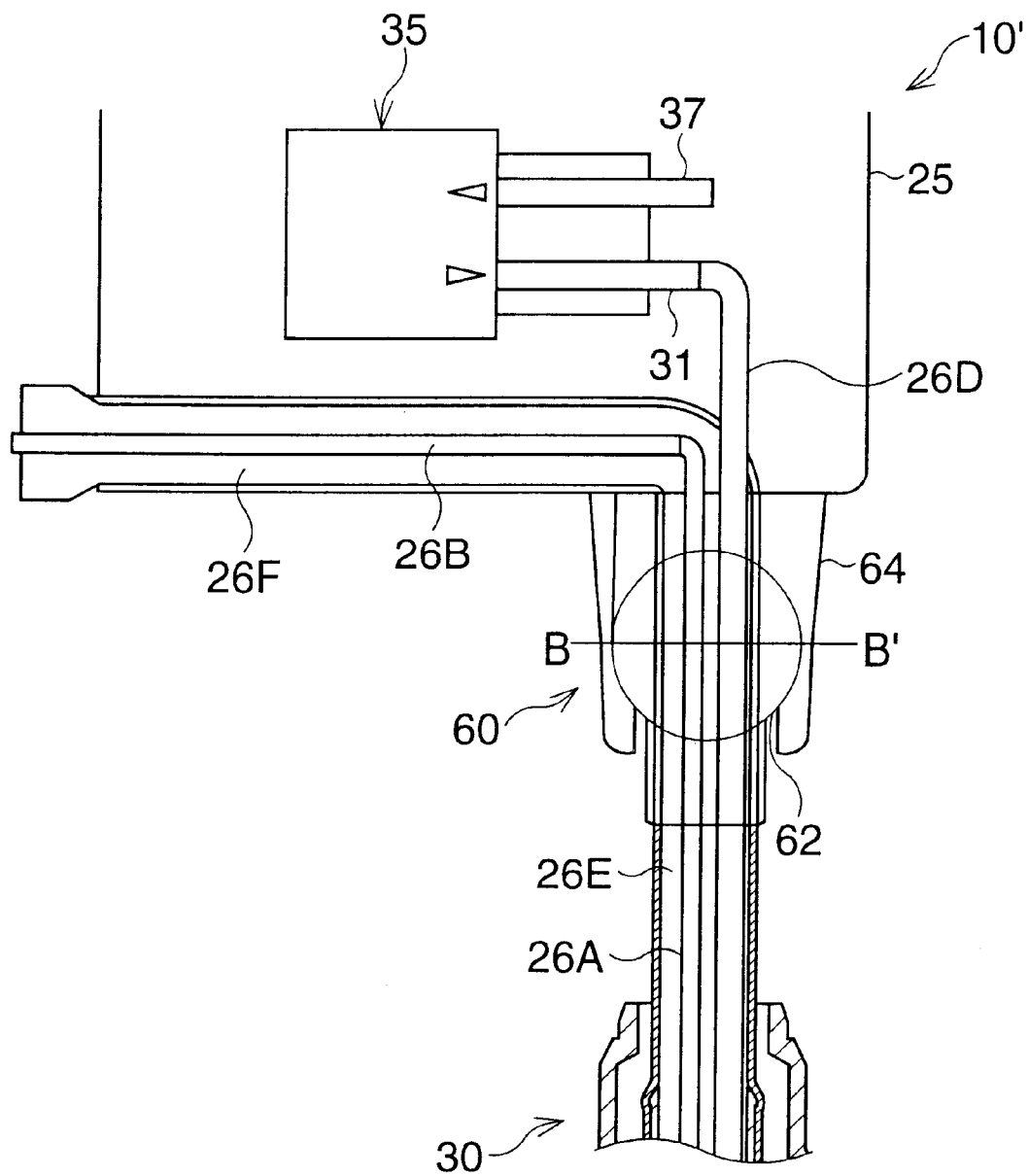
FIG. 7 is a view showing a connecting portion of the bottle and the water and air supply apparatus according to the third embodiment.
Figure 8:
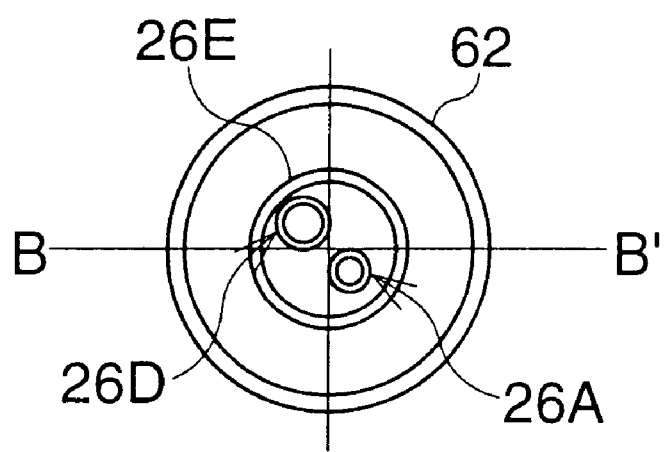
FIG. 8 is a view showing a section view of the connecting portion shown in FIG. 7.

With reference to FIGS. 7 and 8, a third embodiment is explained. The third embodiment is different from the first embodiment in that a ball joint is applied.

FIG. 7 is a view showing a connecting portion associated with the bottle according to the third embodiment. The bottle 30 is attached to the water and air supply apparatus 25 via a ball joint 60. which has a ball member 62 and ball supporter 64.

FIG. 8 is a section view along line B—B' shown in FIG. 7. The water supplying tube 26A and the air supplying tube 26D extend through the air supplying tube 26E. The bottle 30 is pivotable in any direction around a center of the ball member 62.

As for the air-supply, nitrogen or oxygen may be discharged from the tip portion 15 in place of air. In this case, a nitrogen cylinder or oxygen cylinder may be connected to the inlet of the pump 34. Further, as for the water-supply, medicinal liquid may be stored in the bottle 30 in place of water.

In the first, second, and third embodiments, the bottle 30 is attached such that the bottle 30 maintains a level position. However, the bottle 30 may be attached such that the bottle 30 does not incline past a tolerable angle to the vertical direction. Note that, the tolerable angle indicates a maximum angle at which the water is not discharged.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Application No. 2001-263039 (filed on Aug. 31, 2001) which is expressly incorporated herein, by reference, in its entirety.

What is claimed is:

1. A portable endoscope comprising:
    a liquid supplying tube that transmits liquid to the tip of said endoscope;
    a container that is spatially connected to said liquid supplying tube and stores the liquid;
    a gas supplying tube that is connected to an inside space of said container and transmits gas to the tip of said endoscope;
    a liquid and gas supplier that supplies the liquid in said container to said liquid supplying tube and supplies the gas to said gas supplying tube; and
    a holder that holds said container such that said container generally keeps a horizontal position.

2. The portable endoscope of claim 1, wherein said holder allows said container to pivot in accordance with gravity which operates on said container with said liquid.

3. The portable endoscope of claim 1, wherein said holder and said container are arranged along a vertical direction, said holder supporting said container in the vertical direction.

4. The portable endoscope of claim 1, wherein a part of said water supplying tube and a part of said gas supplying tube extend along a vertical direction, and said container has a hole in the upper portion of said container to spatially connect said container with said water supplying tube and said gas supplying tube.

5. The portable endoscope of claim 1, wherein said container is attached to said liquid and gas supplier via said holder.

6. The portable endoscope of claim 1, wherein said liquid and gas supplier is attached to an operating portion of said endoscope.

7. The portable endoscope of claim 1, wherein said liquid and gas supplier has a pump that takes in fresh air and discharges compressed air from the tip of said endoscope.

8. The portable endoscope of claim 1, wherein said holder includes a flexible member that is formed as a tube and holds an upper portion of said container, said flexible member allowing said container to pivot.

9. The portable endoscope of claim 8, wherein a part of said gas supplying tube and a part of said water supplying tube pass through the flexible member.

10. The portable endoscope of claim 1, wherein said holder includes a universal joint that holds said container, said universal joint allowing said container to pivot.

11. The portable endoscope of claim 1, wherein said holder includes a ball joint that holds said container, said ball joint allowing said container to pivot.

12. The portable endoscope of claim 1, wherein said container is formed in the shape of a bottle.

13. A portable endoscope comprising:
    a liquid supplying tube that transmits liquid to the tip of said endoscope;
    a container that is spatially connected to said liquid supplying tube and stores the liquid;
    a gas supplying tube that is connected to an inside space of said container and transmits gas to the tip of said endoscope;
    a liquid and gas supplier that supplies the liquid in said container to said liquid supplying tube and supplies the gas to said gas supplying tube; and
    a holder that holds said container such that said container keeps one predetermined position with respect to a vertical direction.

* * * * *